US010602935B2

(12) United States Patent
Fuke et al.

(10) Patent No.: US 10,602,935 B2
(45) Date of Patent: Mar. 31, 2020

(54) INFORMATION PROCESSING APPARATUS, METHOD AND STORAGE MEDIUM

(71) Applicant: TDK Corporation, Tokyo (JP)

(72) Inventors: Sawa Fuke, Kanagawa (JP); Junya Takakura, Kanagawa (JP); Yasunobu Yamauchi, Kanagawa (JP); Kanako Nakayama, Tokyo (JP); Takuji Suzuki, Kanagawa (JP)

(73) Assignee: TDK CORPORATION, Tokyo (JP)

( * ) Notice: Subject to any disclaimer, the term of this patent is extended or adjusted under 35 U.S.C. 154(b) by 700 days.

(21) Appl. No.: 14/850,245

(22) Filed: Sep. 10, 2015

(65) Prior Publication Data

US 2016/0213266 A1 Jul. 28, 2016

(30) Foreign Application Priority Data

Jan. 22, 2015 (JP) ................................. 2015-010250

(51) Int. Cl.
*A61B 5/021* (2006.01)
*A61B 5/00* (2006.01)
(Continued)

(52) U.S. Cl.
CPC ........ *A61B 5/02108* (2013.01); *A61B 5/0004* (2013.01); *A61B 5/0022* (2013.01);
(Continued)

(58) Field of Classification Search
None
See application file for complete search history.

(56) References Cited

U.S. PATENT DOCUMENTS 5,755,229 A * 5/1998 Amano .............. A61B 5/02007
600/500
6,110,109 A * 8/2000 Hu ........................ G16H 50/20
600/300
(Continued)

FOREIGN PATENT DOCUMENTS

JP H11-299740 A 11/1999
JP 2003-111734 4/2003
(Continued)

OTHER PUBLICATIONS

"Blood Test." Merriam-Webster.com. Merriam-Webster, Web. Mar. 8, 2018.*

(Continued)

*Primary Examiner* — Kaylee R Wilson
*Assistant Examiner* — Jairo H Portillo
(74) *Attorney, Agent, or Firm* — Oliff PLC

(57) ABSTRACT

According to one embodiment, an information processing apparatus includes an acquisition module, a feature calculator and a blood pressure value calculator. The acquisition module is configured to acquire a basic first attribute of a user, a second attribute related to a physique of the user, a third attribute related to a circulatory organ of the user, and a biological signal related to a living body of the user. The feature calculator is configured to calculate a feature in the biological signal. The blood pressure value calculator is configured to calculate a blood pressure value of the user, based on the first attribute, the second attribute, the third attribute, and the feature.

16 Claims, 10 Drawing Sheets

(51) Int. Cl.
    *G16H 40/63*     (2018.01)
    *G16H 50/20*     (2018.01)
    *A61B 5/0402*     (2006.01)
    *A61B 5/107*     (2006.01)

(52) U.S. Cl.
    CPC .......... *A61B 5/0046* (2013.01); *A61B 5/0077* (2013.01); *A61B 5/0402* (2013.01); *A61B 5/1075* (2013.01); *A61B 5/6801* (2013.01); *A61B 5/7278* (2013.01); *A61B 5/742* (2013.01); *G16H 40/63* (2018.01); *G16H 50/20* (2018.01); *A61B 5/1072* (2013.01); *A61B 5/1079* (2013.01); *A61B 2562/0219* (2013.01)

(56) References Cited

U.S. PATENT DOCUMENTS

| | | | | |
|---|---|---|---|---|
| 2005/0187437 | A1* | 8/2005 | Matsugu | A61B 5/16 600/301 |
| 2006/0200011 | A1 | 9/2006 | Suzuki et al. | |
| 2007/0068539 | A1* | 3/2007 | Hall | G16H 15/00 128/898 |
| 2007/0167844 | A1* | 7/2007 | Asada | A61B 5/022 600/485 |
| 2007/0293773 | A1* | 12/2007 | Ghigini | A61B 5/022 600/485 |
| 2008/0249382 | A1 | 10/2008 | Oh et al. | |
| 2009/0125324 | A1 | 5/2009 | Keravich et al. | |
| 2009/0149763 | A1* | 6/2009 | Chen | A61B 5/02116 600/494 |
| 2010/0049059 | A1 | 2/2010 | Ha et al. | |
| 2010/0113890 | A1* | 5/2010 | Cho | A61B 5/0402 600/301 |
| 2010/0179389 | A1* | 7/2010 | Moroney, III | G16H 40/63 600/301 |
| 2010/0312115 | A1* | 12/2010 | Dentinger | A61B 5/02116 600/450 |
| 2011/0196244 | A1 | 8/2011 | Ribas Ripoll et al. | |
| 2012/0283584 | A1* | 11/2012 | Yu | A61B 5/02208 600/493 |
| 2013/0345573 | A1* | 12/2013 | Kargar | A61B 5/021 600/485 |
| 2014/0171805 | A1* | 6/2014 | Mullin | H05K 13/00 600/474 |
| 2015/0313608 | A1* | 11/2015 | Baudenbacher | A61B 17/1355 601/150 |

FOREIGN PATENT DOCUMENTS

| | | |
|---|---|---|
| JP | 2006-212218 A | 8/2006 |
| JP | 2008-521460 A | 6/2008 |
| JP | 2009-89829 | 4/2009 |
| JP | 4342455 | 10/2009 |
| JP | 2010-046494 A | 3/2010 |
| JP | 2010-220690 A | 10/2010 |
| JP | 2010-239992 A | 10/2010 |
| JP | 2011-503722 | 1/2011 |
| JP | 2012-505679 | 3/2012 |
| JP | 2014-000105 | 1/2014 |
| JP | 2014-81954 | 5/2014 |
| JP | 2014-230671 A | 12/2014 |
| WO | WO-2013/001265 | 1/2013 |

OTHER PUBLICATIONS

Extended European Search Report dated Jun. 17, 2016, in counterpart European Application No. 15184743.1; 8 pages.

\* cited by examiner

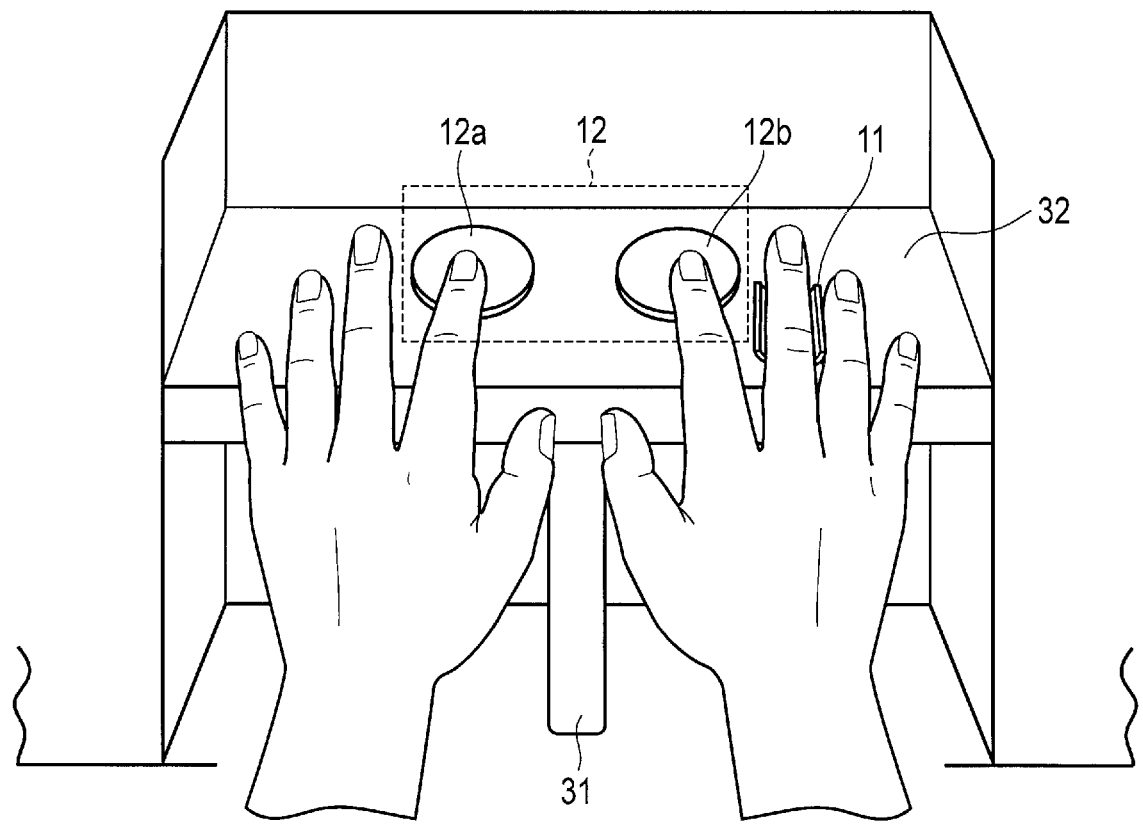
F I G. 3
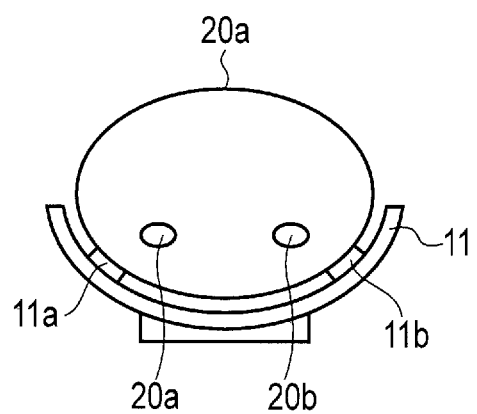
F I G. 4

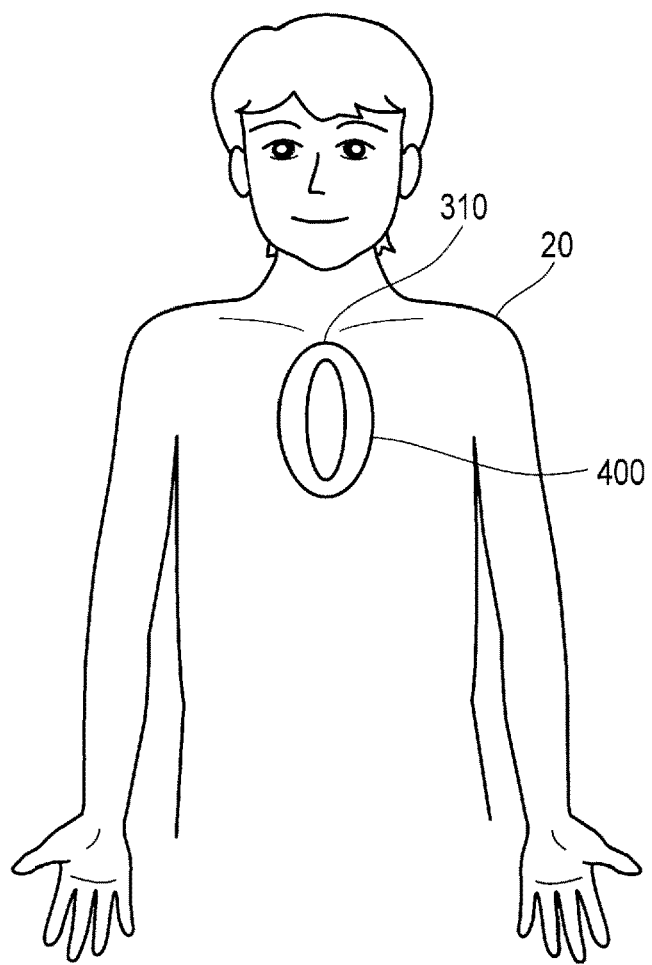
F I G. 13
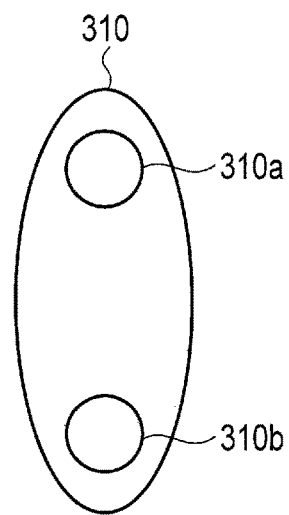
F I G. 14

INFORMATION PROCESSING APPARATUS, METHOD AND STORAGE MEDIUM

CROSS-REFERENCE TO RELATED APPLICATIONS

This application is based upon and claims the benefit of priority from Japanese Patent Application No. 2015-010250, filed Jan. 22, 2015, the entire contents of which are incorporated herein by reference.

FIELD

Embodiments described herein relate generally to an information processing apparatus, method and a storage medium.

BACKGROUND

In general, blood pressure is periodically measured for maintaining and managing health. In the measurement of blood pressure, a cuff blood pressure meter is often used.

According to the cuff blood pressure meter, for example, blood pressure in an artery of an upper arm of a target can be measured by winding a belt called a cuff around the upper arm of the target.

However, when the above-described cuff blood pressure meter is used, the upper arm is pressurized by the cuff, whereby a burden on the target is large.

Thus, a technique which enables a blood pressure value to be easily obtained with a light burden on a target has been desired.

BRIEF DESCRIPTION OF THE DRAWINGS

FIG. 3 is a diagram showing an example of an overview of a biological signal measurement module.

FIG. 4 is a cross-sectional view of a first measurement module.

FIG. 13 is a diagram showing an example of how a biological sensor apparatus is used.

FIG. 14 is a diagram showing an example of an attachment surface of the biological sensor apparatus.

DETAILED DESCRIPTION

Various embodiments will be described hereinafter with reference to the accompanying drawings.

In general, according to one embodiment, an information processing apparatus includes an acquisition module, a feature calculator and a blood pressure value calculator. The acquisition module is configured to acquire a basic first attribute of a user, a second attribute related to a physique of the user, a third attribute related to a circulatory organ of the user, and a biological signal related to a living body of the user. The feature calculator is configured to calculate a feature in the biological signal. The blood pressure value calculator is configured to calculate a blood pressure value of the user, based on the first attribute, the second attribute, the third attribute, and the feature.

First Embodiment

Figure 1:
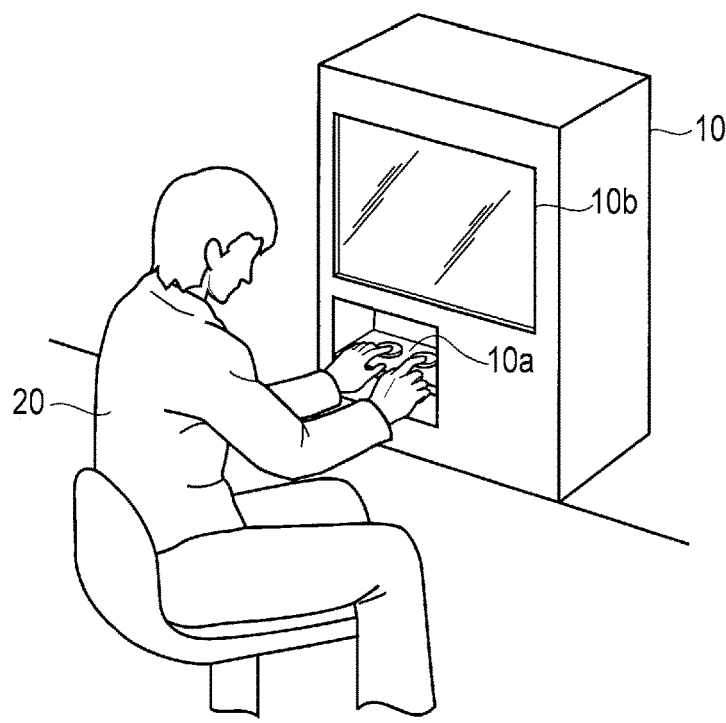
FIG. 1 is a diagram showing an example of an outside of a blood pressure calculation apparatus according to a first embodiment.

First, a first embodiment will be described. FIG. 1 shows an example of an outside of a blood pressure calculation apparatus according to the present embodiment. The blood pressure calculation apparatus 10 shown in FIG. 1 is, for example, an information processing apparatus used to calculate (estimate) a blood pressure value (for example, a systolic blood pressure value) of a user (target) 20 seated at a position facing the blood pressure calculation apparatus 10.

A main body of the blood pressure calculation apparatus 10 includes a housing in the shape of a box. As shown in FIG. 1, the main body of the blood pressure calculation apparatus 10 is provided with a biological signal measurement module 10a and a touchscreen display 10b.

The biological signal measurement module 10a is configured to measure biological signals related to a living body of the user 20. Biological signals measured by the biological signal measurement module 10a include, for example, pulse wave signals and electrocardiographic signals. In the touchscreen display 10b, a touchpanel and a flat panel display, for example, a liquid crystal display (LCD), are incorporated. The touchscreen display 10b is thereby used as an input/output device in the blood pressure calculation apparatus 10.

Although not shown in FIG. 1, the blood pressure calculation apparatus 10 is communicably connected to, for example, an external server (external device) which manages various items of data on the user 20. In the present embodiment, a blood pressure calculation system includes the blood pressure calculation apparatus 10 and the external server connected to the blood pressure calculation apparatus 10. The blood pressure calculation apparatus 10 may be configured to be connected to external servers.

An administrator of the blood pressure calculation apparatus 10 (blood pressure calculation system) according to the present embodiment is assumed to be a medical institution, for example, a hospital. In this case, the blood pressure calculation apparatus 10 can calculate (estimate) a blood pressure value of the user 20 while the user 20 is waiting or arranging for an examination at a waiting room of the medical institution, and for example, the calculated blood pressure value can be provided to the user 20, a doctor, or the like, as an index of condition before the examination. The administrator of the blood pressure calculation apparatus 10 may be a health management group of a company, a retail store such as a drugstore or a supermarket, a vending machine company, etc.

Figure 2:
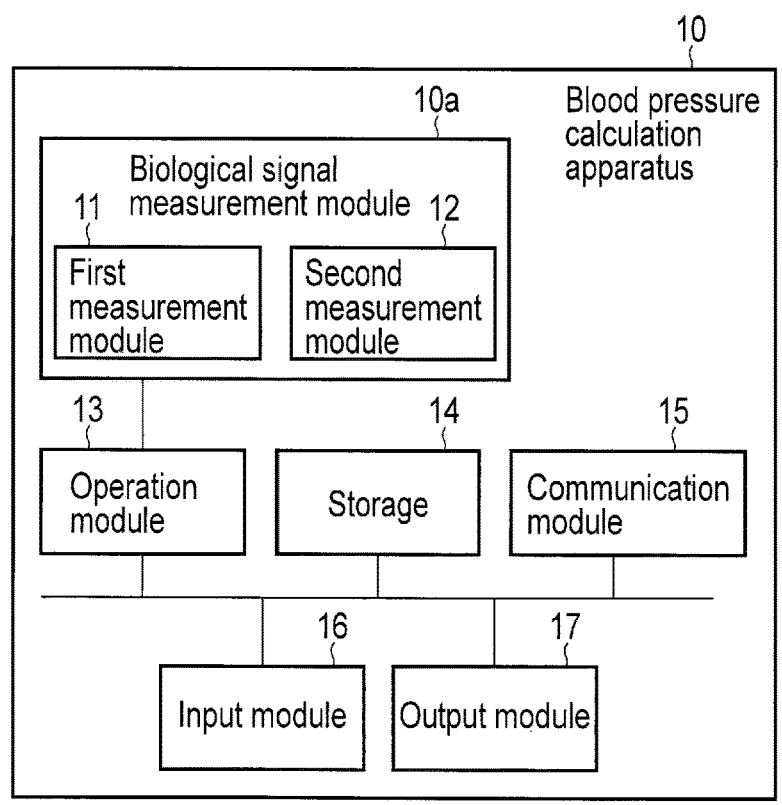
FIG. 2 is a diagram showing an example of a system configuration of the blood pressure calculation apparatus.

FIG. 2 shows an example of a system configuration of the blood pressure calculation apparatus 10 shown in FIG. 1. As shown in FIG. 2, the blood pressure calculation apparatus 10 includes a first measurement module 11, a second measurement module 12, an operation module 13, a storage 14, a communication module 15, an input module 16, an output module 17, etc.

The first measurement module 11 and the second measurement module 12 are included in the biological signal measurement module 10a shown in FIG. 1. Here, the biological signal measurement module 10a (the first measurement module 11 and the second measurement module 12) will be described in detail with reference to FIG. 3 and FIG. 4. FIG. 3 shows an example of an overview of the biological signal measurement module 10a. FIG. 4 is a cross-sectional view of the first measurement module 11.

As shown in FIG. 3, the first measurement module 11 and the second measurement module 12 are placed on a placement surface 32 supported by a lower end 31.

The first measurement module 11 includes a pulse sensor configured to measure, for example, a pulse wave signal (first pulse wave signal) related to a pulse wave at ventral surface of a fingertip (first body surface position) of the user 20.

Specifically, as shown in FIG. 4, the first measurement module 11 has, for example, a semicylinder shape, and a light emitter 11a and a light receiver 11b (photoelectric unit) are provided on a top surface of the first measurement module 11. The light emitter 11a is configured to radiate light to ventral surface of a fingertip 20a of the user 20 placed on the first measurement module 11. The light receiver 11b is placed at a position where it can detect light which is emitted by the light emitter 11e and is transmitted through the fingertip 20a of the user 20.

Here, light transmitted through the fingertip 20a of the user 20 is affected by a change in bloodstream in a blood capillary 20b at ventral surface of a fingertip 20a. Such light is detected by the light receiver 11b, whereby the first measurement module 11 can measure a pulse wave signal according to a change in bloodstream in the artery 20b.

The light receiver 11b may be placed at, for example, a position where it is adjacent to the light emitter 11a. In this case, reflected light of light emitted by the light emitter 11a is detected by the light receiver 11b, whereby a pulse wave signal can be measured.

On the other hand, the second measurement module 12 includes an electrocardiographic sensor configured to measure, for example, an electrocardiographic signal related to the electrical activity of the heart of the user 20.

Specifically, as shown in FIG. 3, the second measurement module 12 includes electrocardiographic electrodes 12a and 12b. The electrocardiographic electrode 12a is placed at a position touched by the left hand's finger (for example, a left index finger) of the user 20. The electrocardiographic electrode 12b is placed at a position touched by the right hand's finger (for example, a right index finger) of the user 20. The second measurement module 12 can measure an electrocardiographic signal by analyzing time-series signals of a potential difference between the electrocardiographic electrodes 12a and 12b touched by the left hand's finger and the right hand's finger of the user 20.

Although it has been herein explained that the biological signal measurement module 10a includes the first measurement module 11 (pulse sensor) and the second measurement module 12 (electrocardiographic sensor), the biological signal measurement module 10a may include other sensors (biological sensors). For example, a temperature sensor which measures a body surface temperature of the user 20 and an $SpO_2$ sensor which measures a blood oxygen level of the user 20 may be included in the biological signal measurement module 10a.

It is assumed that the lower end 31 supporting the placement surface 32 on which the first measurement module 11 and the second measurement module 12 are placed can move the placement surface 32, for example, up and down (that is, change the position of the placement surface 32). Thus, a measured position (that is, the positions of the first measurement module 11 and the second measurement module 12) can be adjusted in accordance with, for example, a physique of the user 20.

The operation module 13 includes a processor which controls operation of various components in the blood pressure calculation apparatus 10. The operation module 13 executes various computer programs stored in the storage 14.

The storage 14 includes storage media, for example, a ROM and a RAM. The storage 14 stores various items of data used to execute the computer programs, etc., as well as the above-described computer programs.

The communication module 15 is configured to communicate wirelessly through, for example, a wireless LAN. The communication module 15 includes a transmitter configured to transmit a signal and a receiver configured to receive a signal through, for example, a network such as the Internet. By the communication module 15, the blood pressure calculation apparatus 10 is connected to an external server through the network.

The external server connected to the blood pressure calculation apparatus 10 through the network includes, for example, an electronic medical record server which manages data on the user 20 (hereinafter, referred to as user attribute data). User attribute data managed by the electronic medical record server includes data on an electronic medical record of the user 20, data on a result of a general medical examination, data on a result of a periodical medical checkup, etc. The blood pressure calculation apparatus 10 can acquire age, sex, height, weight and blood test result of the user 20 from user attribute data managed by the electronic medical record server by referring to the electronic medical record server based on identification data for identifying the user 20 (hereinafter, referred to as user ID).

The input module 16 is configured to input various items of data in accordance with the user's operation. The input module 16 is implemented as, for example, the touchpanel incorporated in the touchscreen display 10b shown in FIG. 1, but may be implemented as an input key, etc. Moreover, the input module 16 may be an IC card reader, a magnetic card reader, or the like for reading the above-described user ID.

The output module 17 is configured to output, for example, a blood pressure (value) of the user 20 calculated by the blood pressure calculation apparatus 10. The output module 17 is implemented as, for example, the display incorporated in the touchscreen display 10b shown in FIG. 1.

Figure 5:
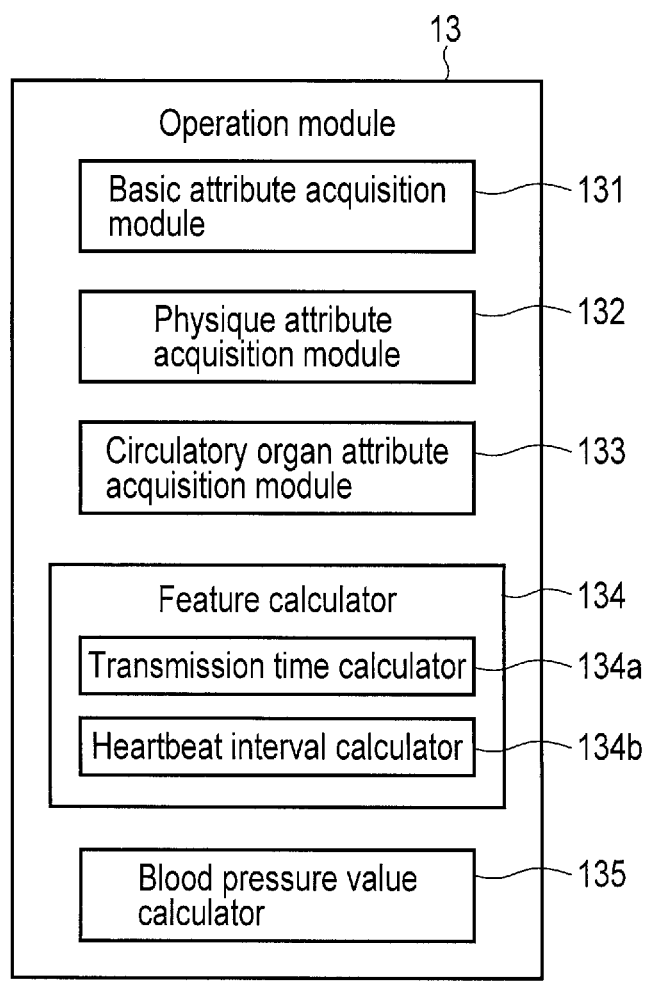
FIG. 5 is a block diagram showing an example of a functional configuration of an operation module.

FIG. 5 is a block diagram showing a functional configuration of the operation module 13 shown in FIG. 2. As shown in FIG. 5, the operation module 13 includes a basic attribute acquisition module 131, a physique attribute acquisition module 132, a circulatory organ attribute acquisition module 133, a feature calculator 134, and a blood pressure value calculator 135.

In the present embodiment, some or all of the modules 131 to 135 are implemented when the operation module 13 executes a computer program, that is, they are implemented as software. Some or all of the modules 131 to 135 may be implemented as hardware such as an integrated circuit (IC), and may be implemented as a combined structure of software and hardware.

The basic attribute acquisition module 131 acquires a basic attribute of the user 20 (hereinafter, referred to as a basic attribute). Specifically, the basic attribute acquisition module 131 refers to user attribute data managed by an external server based on the user ID for identifying the user 20, and acquires (receives), for example, the age and sex of the user 20 from the external server as basic attributes. The user ID used to acquire a basic attribute is input through the above-described input module 16. As the user ID, a medical record number, an employee number, an insurance number or the like assigned to the user 20 can be used.

As well as the age and sex of the user 20, race, disease history, drinking history, smoking history, etc., of the user 20 may be acquired as basic attributes. These can also be acquired from the above-described external server. That is, it suffices if the basic attribute acquisition module 131 is configured to acquire, for example, at least one of the age, the sex, the race, the disease history, the drinking history, and the smoking history of the user 20, as a basic attribute.

In addition, a basic attribute may be acquired from an external device other than an external server, for example, a smartphone, a wearable device, or a healthcare device possessed by the user. Moreover, a basic attribute input by the input module 16 in accordance with the user's 20 operation may be acquired.

The physique attribute acquisition module 132 acquires an attribute related to the physique of the user 20 (hereinafter, referred to as a physique attribute). Specifically, the physique attribute acquisition module 132 refers to user attribute data managed by an external server based on the user ID for identifying the user 20, and acquires (receives), for example, a body mass index (EMI) value which is an index value indicating the degree of corpulence of the user 20 from the external server as a physique attribute.

An index value indicating the degree of corpulence of the user 20 acquired as a physique attribute may be, for example, a body adiposity index (BAI) value, the degree of corpulence, or body fat percentage. That is, it suffices if the physique attribute acquisition module 132 is configured to acquire, for example, at least one of the BMI value, the BAI value, the degree of corpulence, and the body fat percentage, as a physique attribute.

In addition, a physique attribute may be calculated from user attribute data managed by an external server. Specifically, the physique attribute acquisition module 132, for example, may receive the height and the weight of the user 20 from an external server, and calculate a BMI value from the height and the weight. Moreover, the physique attribute acquisition module 132 may calculate the degree of corpulence based on a BMI value. In addition, the physique attribute acquisition module 132 may calculate a BAI value based on the height and the hip circumference of the user 20.

As well as those described above, an index value related to a metabolic syndrome, etc., may be acquired from an external server as a physique attribute. In addition, the index value related to a metabolic syndrome may be calculated from the height and the abdominal circumference of the user 20 acquired from the external server.

It has been herein explained that an index value indicating the degree of corpulence of the user 20, for example, is acquired as a physique attribute. However, the physique attribute acquisition module 132 may acquire an actual regional length of a body region such as the abdominal circumference, the neck circumference, or the hip circumference of the user which is considered to be highly associated with corpulence, as a physique attribute instead of the index value. In other words, the physique attribute acquisition module 132 may acquire, for example, at least one of the neck circumference, the abdominal circumference, and the hip circumference of the user 20, as a physique attribute.

The above-described physique attributes may be acquired from an external device other than an external server, for example, a smartphone, a wearable device, or a healthcare device possessed by the user. Moreover, a physique attribute input by the input module 16 in accordance with the user's 20 operation may be acquired. Furthermore, a physique attribute may be calculated from data managed by a smartphone, a wearable device or a healthcare device, or data input by the input module 16 (for example, the height, the weight, the abdominal circumference, or the hip circumference of the user 20).

The circulatory organ attribute acquisition module 133 acquires an attribute related to the circulatory organ of the user 20 (hereinafter, referred to as a circulatory organ attribute). Specifically, the circulatory organ attribute acquisition module 133 refers to user attribute data managed by an external server based on the user ID for identifying the user 20, and acquires (receives), for example, a blood total cholesterol value which is a blood test result of the user 20, from the external server as a circulatory organ attribute.

As well as the blood total cholesterol value, a low density lipoprotein (LDL) cholesterol value, a high density lipoprotein (HDL) cholesterol value, a neutral fat value, a baPWV value, a cardio ankle vascular index (CAVI) value, etc., may be acquired as circulatory organ attributes. These can also be acquired from the above-described external server. That is, it suffices if the circulatory organ attribute acquisition module 133 is configured to acquire, for example, at least one of the blood total cholesterol value, the LDL cholesterol value, the HDL cholesterol value, the neutral fat value, the baPWV value, and the CAVI value, as a circulatory organ attribute. The blood total cholesterol value, the LDL cholesterol value, the HDL cholesterol value, the neutral fat value, the baPWV value, and the CAVI value, which are acquired as circulatory organ attributes, are values related to arteriosclerosis (for example, the elasticity of an artery or the diameter of an artery).

In addition, a circulatory organ attribute may be calculated from user attribute data managed by an external server.

Moreover, a circulatory organ attribute may be acquired from an external device other than an external server, for example, a smartphone, a wearable device, a healthcare device, or medical equipment possessed by the user. In addition, a circulatory organ attribute input by the input module 16 in accordance with the user's 20 operation may be acquired.

The feature calculator 134 calculates a feature in biological signals measured by (the first measurement module 11 and the second measurement module 12 included in) the biological signal measurement module 10a. The feature calculator 134 includes a transit time calculator 134a and a heartbeat interval calculator 134b.

The transit time calculator 134a calculates a pulse wave transit time as a feature, based on a pulse wave signal measured by the first measurement module 11 and an electrocardiographic signal measured by the second measurement module 12.

The heartbeat interval calculator 134b calculates a heartbeat interval or a heart rate as a feature, based on a pulse wave signal measured by the first measurement module 11 or an electrocardiographic signal measured by the second measurement module 12.

The blood pressure value calculator 135 calculates a blood pressure value of the user 20 based on a basic attribute (value) acquired by the basic attribute acquisition module 131, a physique attribute (value) acquired by the physique attribute acquisition module 132, a circulatory organ attribute (value) acquired by the circulatory organ attribute acquisition module 133, and a feature calculated by the feature calculator 134. In this case, the blood pressure value calculator 135 calculates the blood pressure value, using parameters (values) calculated in advance as will be described later.

A blood pressure value calculated by the blood pressure value calculator 135 is output by the output module 17. Specifically, a blood pressure value calculated by the blood pressure value calculator 135 is displayed, for example, on a screen of the display.

Next, a procedure of the blood pressure calculation apparatus 10 according to the present embodiment will be described with reference to the flowchart of FIG. 6. In the following description, the user 20 using the blood pressure calculation apparatus 10 will be referred to as the target user 20 for convenience.

When using the blood pressure calculation apparatus 10, the target user 20 designates the user ID for identifying the target user 20 (hereinafter, referred to as target user ID), for example, by operating the above-described touchpanel. As the user ID, for example, a medical record number, an employee number, or an insurance number can be designated. The input module 16 thereby inputs the target user ID (step S1). The target user ID may be input by, for example, an IC card reader or a magnetic card reader.

Next, (the operation module 13 provided in) the blood pressure calculation apparatus 10 accesses an external server such as an electronic medical record server communicably connected to the blood pressure calculation apparatus 10, and refers to user attribute data (data on an electronic medical record, a result of a general medical examination, and a result of a periodical medical checkup) of the target user 20 managed by the external server based on the target user ID input by the input module 16.

The basic attribute acquisition module 131 thereby acquires a basic attribute (first attribute) of the target user 20 from (user attribute data managed by) the external server (step S2). Basic attributes acquired by the basic attribute acquisition module 131 include, for example, the age and sex of the target user 20.

In addition, the physique attribute acquisition module 132 acquires a physique attribute (second attribute) of the target user 20 from (user attribute data managed by) the external server (step S3). Physique attributes acquired by the physique attribute acquisition module 132 include, for example, a BMI value of the target user 20.

Moreover, the circulatory organ attribute acquisition module 133 acquires a circulatory organ attribute (third attribute) of the target user 20 from (user attribute data managed by) the external server (step S3). Circulatory organ attributes acquired by the circulatory organ attribute acquisition module 133 include, for example, a blood total cholesterol value of the target user 20.

Here, the target user 20 places, for example, ventral surface of the right hand's middle finger on the first measurement module 11 as shown in FIG. 3. The first measurement module 11 thereby can measure a pulse wave signal (photoelectric pulse waveform) related to a pulse wave of the target user 20. Moreover, the target user 20 touches, for example, the left hand's index finger to the electrocardiographic electrode 12a included in the second measurement module 12, and touches, for example, the right hand's index finger to the electrocardiographic electrode 12b included in the second measurement module 12. The second measurement module 12 thereby can measure an electrocardiographic signal (electrocardiographic waveform) related to the electrical activity of the heart of the target user 20.

The feature calculator 134 acquires a pulse wave signal measured by the first measurement module 11 and an electrocardiographic signal measured by the second measurement module 12 (that is, biological signals of the target user 20) (step S5).

The transit time calculator 134a included in the feature calculator 134 calculates a pulse wave transit time (PWTT) from the acquired pulse wave signal and electrocardiographic signal as a feature in the biological signals of the target user 20 (step S6).

Here, a pulse wave transit time calculated by the transit time calculator 134a will be described with reference to FIG. 7. It is herein assumed that a pulse wave signal (pulse waveform) 41 is measured by the first measurement module 11, and an electrocardiographic signal (electrocardiographic waveform) 42 is measured by the second measurement module 12.

In this case, the transit time calculator 134a calculates a difference 43a between a peak time 42a of an R wave of the electrocardiographic signal 42 and a time 41a of a rising point of the pulse wave signal 41. Similarly, the transit time calculator 134a calculates a difference 43b between a peak time 42b of the R wave of the electrocardiographic signal 42 and a time 41b of a rising point of the pulse wave signal 41.

The transit time calculator 134a calculates a mean difference between the peak time of the R wave of the electrocardiographic signal 42 and the time of the rising point of the pulse wave signal 41 calculated in a predetermined period (measuring period) as a pulse wave transit time. In other words, the transit time calculator 134a outputs a value obtained by averaging pulse wave transit times of all the pulses in a predetermined section (measuring period).

Although it has been herein explained that a pulse wave transit time is calculated from a pulse wave signal measured by the first measurement module 11 and an electrocardiographic signal measured by the second measurement module 12, the second measurement module 12 may measure a pulse wave signal (second pulse wave signal) similarly to the first measurement module 11. When the second measurement module 12 measures a pulse wave signal, the second measurement module 12 measures a pulse wave signal at a measured region (second body surface position) different from that of the first measurement module 11. Specifically, when the first measurement module 11 measures a pulse wave signal in the vicinity of a first joint of a finger of the target user 20, the second measurement module 12 measures a pulse wave signal in the vicinity of a second joint of the same finger. The second measurement module 12 may measure a pulse wave signal at, for example, the back of a hand or an arm of the target user 20, as long as the pulse wave signal is measured at a body surface position different from that of the first measurement module 11. In addition, pulse wave signals acquired by the first measurement module 11 and the second measurement module 12 may not be signals measured photoelectrically, but may be, for example, signals measured by using a radar or a pressure sensor.

According to such a structure, pulse wave signals having a time difference according to measured regions are measured by the first measurement module 11 and the second measurement module 12. In this case, a mean time difference at the same feature point of a pulse wave signal measured by the first measurement module 11 and a pulse wave signal measured by the second measurement module 12 is used as a pulse wave transit time. In other words, the transit time calculator 134a calculates a mean difference between a time of a rising point of a pulse wave signal measured by the first measurement module 11 and a time of a rising point of a pulse wave signal measured by the second measurement module 12 calculated in a measuring period as a pulse wave transit time.

When pulse wave signals are measured by the first measurement module 11 and the second measurement module 12 as described above, the length between respective measured regions of the pulse wave signals is already known, whereby an arterial length is obvious.

Therefore, a pulse wave velocity obtained by dividing the arterial length by a pulse wave transit time calculated in the above-described manner can also be output as a feature.

Returning to FIG. 6 again, the heartbeat interval calculator 134b included in the feature calculator 134 calculates, for example, a heartbeat interval (RRI) from an acquired pulse wave signal (pulse waveform) or electrocardiographic signal (electrocardiographic waveform) as a feature in the biological signals of the target user 20 (step S7).

Figure 7:
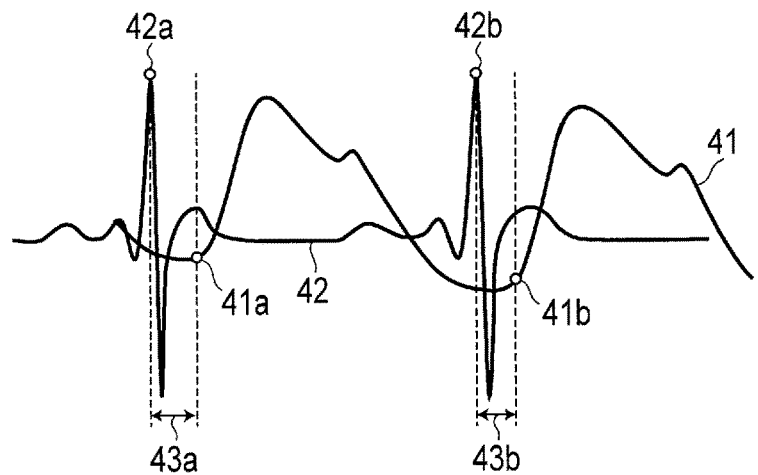
FIG. 7 is a diagram for explaining a pulse wave transit time.

As shown in FIG. 7 above, a predetermined change (for example, a rise of a pulse waveform) occurs in a pulse wave signal in accordance with the heartbeat (that is, pulsation of the heart) of the target user 20. Similarly, a predetermined change (for example, an R wave) occurs in an electrocardiographic signal in accordance with the heartbeat of the target user 20. Thus, the heartbeat interval calculator 134b can calculate a heartbeat interval based on an interval between these changes in a pulse wave signal or an electrocardiographic signal, etc. The heartbeat interval calculator 134b outputs a value obtained by averaging heartbeat intervals calculated in a predetermined period (measuring period).

Here, a systolic blood pressure value is generally estimated based on a pulse wave transit time or a pulse wave velocity. When a blood pressure value is estimated from the pulse wave velocity, it is affected by various arterial functions. Specifically, for example, when we denote the thickness of an arterial wall by h, the inner diameter of an artery by D, and an incremental arterial elastic modulus by EI, a pulse wave velocity PWV is modeled as EI*h/D by Moens-Korteweg equation. In addition, the incremental arterial elastic modulus is modeled as being proportional to the amount of fluctuations in blood pressure. However, it is hard to measure the thickness of an arterial wall, the inner diameter of an artery, an arterial elastic modulus, etc.

On the other hand, for example, with respect to age, which is one of the basic attributes, even in an ordinary target, an arterial wall increases linearly and the elasticity of an artery decreases from his or her twenties to nineties. In addition, when a BMI value (physique attribute) and a blood total cholesterol value (circulatory organ attribute) associated with the amount of fat are high, the inner diameter of a blood vessel is small and the amount of bloodstream decreases. That is, the above-described basic attributes, physique attributes, and circulatory organ attributes are closely associated with a condition of an artery.

Thus, in the present embodiment, the blood pressure value calculator 135 calculates (estimates) a blood pressure value (systolic blood pressure value) of the target user 20, using the above-described mean pulse wave transit time (MPWTT), mean heartbeat interval (MRRI), basic attribute (P1), physique attribute (P2), and circulatory organ attribute (P3) as input (step S8).

In the present embodiment, for example, the following calculating expression is used in the calculation of a blood pressure value by the blood pressure value calculator 135:

$$\alpha1*MPWTT+\alpha2*MRRI+\alpha3*P1+\alpha4*P2+\alpha5*P3+\alpha6$$

This calculating expression is, for example, a regression expression obtained by carrying out a multiple regression analysis, using the above-described pulse wave transit time (MPWTT) and heartbeat interval (MRRI) which are calculated by the transit time calculator 134a and the heartbeat interval calculator 134b, respectively, while a systolic absolute blood pressure value is measured by a cuff blood pressure meter (for example, for thirty seconds), a basic attribute (P1) such as age, a physique attribute (P2) such as a BMI value, and a circulatory organ attribute (P3) such as a blood total cholesterol value, as input variables (explanatory variables), and using the above-described systolic absolute blood pressure value as a response variable.

Parameters (coefficients) $\alpha1$ to $\alpha6$ of the calculating expression obtained by conducting the above-described multiple regression analysis are stored (saved) in advance in, for example, the storage 14.

That is, in the present embodiment, a blood pressure value of the target user 20 is calculated by applying a pulse wave transit time (MPWTT), a heartbeat interval (MRRI), a basic attribute (P1), a physique attribute (P2), and a circulatory organ attribute (P3) obtained by carrying out the above-described processes of steps S2 to S7, and the parameters $\alpha1$ to $\alpha6$ stored in the storage 14, to the above-described calculating expression.

Changes in the elasticity of an artery made with age are caused by a hormone, and there are differences between the sexes. Thus, parameters according to the sexes may be calculated and stored in the storage 14 so that parameters suitable for sex acquired as a basic attribute are used to calculate a blood pressure value of the target user 20.

In addition, when a pulse wave velocity is calculated as described above, the pulse wave velocity may be used in the above-described expression instead of a pulse wave transit time.

The above-described calculating expression is an example, and in the present embodiment, it suffices if a blood pressure value of the user 20 is calculated based on a basic attribute, a physique attribute, a circulatory organ attribute, and a feature mount in biological signals. The blood pressure value of the user 20 may be calculated by other calculating expressions, etc.

When a blood pressure value of the target user 20 is calculated by the blood pressure value calculator 135 as described above, the blood pressure value is output through, for example, the output module 17 (step S9). Specifically, the blood pressure value of the target user 20 is displayed on, for example, the screen of the display. In this case, a pulse wave transit time calculated by the transit time calculator 134a, a heartbeat interval (or a heart rate) calculated by the heartbeat interval calculator 134b, a basic attribute, a physique attribute, a circulatory organ attribute, etc., may be displayed together with the blood pressure value of the target user 20. Moreover, when the biological signal measurement module 10a includes a temperature sensor and an $SpO_2$ sensor, measurement results by the respective sensors (that is, a temperature and a blood oxygen level of the target user 20) may be displayed as health data.

In addition, the blood pressure value, the heart rate, etc., of the target user 20 may be transmitted (that is, uploaded) to an external server (for example, a medical server) through the communication module 15 to be displayed on, for example, a terminal used by a doctor, etc.

As described above, in the present embodiment, a basic attribute (first attribute), a physique attribute (second attribute), and a circulatory organ attribute (third attribute) of the user are acquired, a feature in biological signals related to the living body of the user is calculated, and a blood pressure value of the user 20 is calculated based on the basic attribute, the physique attribute, the circulatory organ attribute, and the feature.

Specifically, in the present embodiment, a pulse wave transit time or a pulse wave velocity is calculated as a feature based on a pulse wave signal (first pulse wave signal) related to a pulse wave at a specific measured region (first body surface position) of the user, and a pulse wave signal (second pulse wave signal) related to a pulse at a measured region (second body surface position) different from the measured region or an electrocardiographic signal related to the electrical activity of the heart. Moreover, in the present embodiment, a heartbeat interval or a heart rate is calculated as a feature based on a pulse wave signal or an electrocardiographic signal.

As a basic attribute, at least one of age, sex, race, disease history, drinking history, and smoking history of the user 20 is acquired from an external server. At least one of the age, the sex, the race, the disease history, the drinking history, and the smoking history of the user 20 input by the input module 16 in accordance with the user's 20 operation may also be acquired as a basic attribute.

As a physique attribute, an index value indicating the degree of a corpulent physique of the user 20 (for example, at least one of a BMI value, a BAI value, the degree of corpulence, and body fat percentage) is acquired from an external server. An index value indicating the degree of a corpulent physique of the user 20 input by the input module 16 in accordance with the user's 20 operation may be acquired as a physique attribute. A physique attribute may be a regional length (for example, a neck circumference, an abdominal circumference, and a hip circumference) of a body region of the user 20.

As a circulatory organ attribute, a blood test result (for example, at least one of a blood total cholesterol value, an HDL cholesterol value, a neutral fat value, a baPWV value, and a CAVI value) of the user 20 is acquired from an external server. A blood test result of the user 20 input by the input module 16 in accordance with the user's 20 operation may be acquired as a circulatory organ attribute.

In the present embodiment, according to such a structure, it is unnecessary to, for example, acquire a biological signal and a blood pressure value measured by a cuff blood pressure meter simultaneously and calibrate parameters used to calculate a blood pressure value individually (per user). That is, in the present embodiment, the user 20 can easily acquire a blood pressure value only by placing, for example, ventral surface of a tip of the right hand's middle finger on the first measurement module 11 and touching fingers to (electrocardiographic electrodes 12a and 12b included in) the second measurement module 12 without using a cuff blood pressure meter.

In addition, in the present embodiment, a blood pressure value calculated by the blood pressure calculation apparatus 10 is displayed, whereby the user 20 can easily check his or her blood pressure value. Further, a blood pressure value calculated by the blood pressure calculation apparatus 10 is transmitted to an external server, whereby the blood pressure value can also be used in the processing of the external server or be displayed on a terminal of a doctor, etc.

The blood pressure calculation apparatus 10 according to the present embodiment may be provided with a camera (imaging device) at a position where the user 20 using the blood pressure calculation apparatus 10 can be imaged (for example, an upper part of the touchscreen display 10b shown in FIG. 1). In this case, the above-described basic attribute and physique attribute can be acquired based on an image (a captured image) of the user 20 imaged by the camera.

Hereinafter, the case where these attributes are acquired based on an image of the user 20 will be described.

First, the case where a basic attribute is acquired based on an image of the user 20 will be described. In this case, a face region of the user 20 is extracted from an image of the user 20 imaged by the camera by using a technique such as pattern matching, and an image feature is calculated from the extracted face region. A basic attribute can be acquired by estimating the age, sex, etc., of the user 20 based on, for example, the image feature calculated in this manner and learning data (clustering scenario) prepared in advance.

Next, the case where a physique attribute is acquired based on an image of the user 20 will be described. In this case, a background differencing process is carried out for images obtained by imaging the user 20 standing in front of the blood pressure calculation apparatus 10 with the camera, and a region estimated to be a human body is extracted. A physique attribute can be acquired by estimating the degree of corpulence, etc., from the area of the extracted region, etc. Moreover, a complexion region around the face region of the user 20 extracted by using a technique such as pattern matching as described above is identified, and a neck circumference estimated from the identified region can also be acquired as a physique attribute. When a depth can be seen from acquired images or when a sensor measuring a depth is provided separately, a physique may be calculated more specifically by using a depth of the user 20.

Although the case where a basic attribute and a physique attribute are acquired based on an image of the user 20 has been herein described, a circulatory organ attribute can also be acquired using an image of the user 20. Specifically, a blood test result, etc., of the user 20 can be acquired by identifying (the user ID for identifying) the user 20 by an image recognition process of an image of the user 20.

In order to improve the accuracy of a blood pressure value calculated (estimated) by the blood pressure calculation apparatus 10 according to the present embodiment, it is herein desirable to measure biological signals (a pulse wave signal and an electrocardiographic signal) at a position (relative position) predetermined with respect to the heart of the user 20. Thus, in the present embodiment, the position of the placement surface 32 may be automatically adjusted by controlling the lower end 31 shown in FIG. 3 above.

Specifically, in the structure in which the blood pressure calculation apparatus 10 is provided with a camera as described above, the position of the heart of the user 20 is estimated from the position of the face of the user 20 included in an image of the user 20 imaged by the camera. Moreover, control is exercised to shift the placement surface 32 (that is, the positions of the first measurement module 11 and the second measurement module 12), such that a relative position (height) of a measured region (for example, both hands of the user 20) with respect to the estimated position of the heart will be a predetermined position (within a predetermined range). Accordingly, even biological signals of users 20 differing in, for example, physique, can be measured at the same relative position with respect to the heart.

Although it has been explained in the present embodiment that the biological signal measurement module 10a is provided in the blood pressure calculation apparatus 10, the biological signal measurement module 10a may be provided outside the blood pressure calculation apparatus 10. Moreover, the blood pressure calculation apparatus 10 according to the present embodiment may not be a fixed apparatus shown in FIG. 1, but may be attached to other apparatuses when used.

Second Embodiment

Next, a second embodiment will be described. Although it has been explained in the above-described first embodiment that a circulatory organ attribute (for example, a blood total cholesterol value, which is a blood test result) is used to calculate a blood pressure value, some users 20 using a blood pressure calculation apparatus 10 have never taken a blood test in a medical checkup, a general medical examination, or the like.

Thus, in the present embodiment, it is assumed that a user 20 whose circulatory organ attribute in the first embodiment is hard to acquire uses the blood pressure calculation apparatus 10.

An outline and a system configuration of the blood pressure calculation apparatus 10 according to the present embodiment are the same as those of the above-described first embodiment, and thus will be explained with reference to FIG. 1 and FIG. 2 as appropriate.

Figure 8:
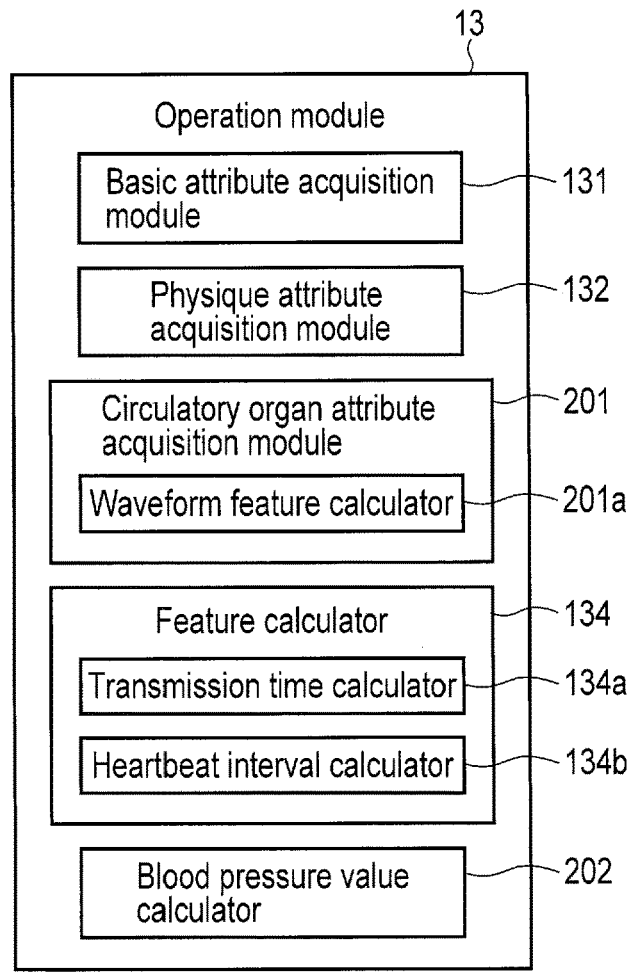
FIG. 8 is a block diagram showing an example of a functional configuration of an operation module in a second embodiment.

FIG. 8 is a block diagram showing a functional configuration of an operation module 13 provided in the blood pressure calculation apparatus 10 according to the present embodiment. In FIG. 8, the same portions as those described above with reference to FIG. 5 are given the same reference numbers, and detailed explanations thereof will be omitted. Portions differing from those of FIG. 5 will be mainly described herein.

As shown in FIG. 8, the operation module 13 includes a circulatory organ attribute acquisition module 201 and a blood pressure value calculator 202. In the present embodiment, it is assumed that either or both of the modules 201 and 202 are implemented as software. Either or both of the modules 201 and 202 may be implemented as hardware, or may be implemented as a combined structure of software and hardware.

The circulatory organ attribute acquisition module 201 includes a waveform feature calculator 201a.

The waveform feature calculator 201a calculates a feature (waveform feature) in a pulse wave signal, based on the pulse wave signal measured by the first measurement module 11.

The circulatory organ attribute acquisition module 201 acquires a waveform feature calculated by the waveform feature calculator 201a as a circulatory organ attribute.

The blood pressure value calculator 202 calculates a blood pressure value of the user 20, using a waveform feature which is acquired by the circulatory organ attribute acquisition module 201 as a substitute for a circulatory organ attribute in the above-described first embodiment.

Figure 9:
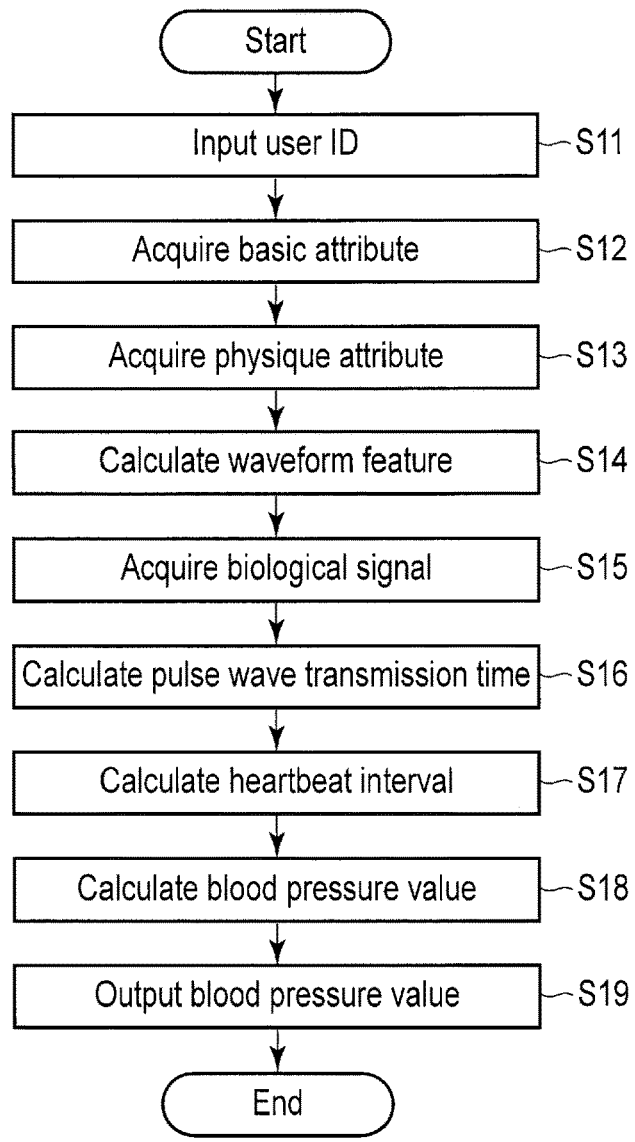
FIG. 9 is a flowchart showing an example of a procedure of the blood pressure calculation apparatus.

Next, a procedure of the blood pressure calculation apparatus 10 according to the present embodiment will be described with reference to the flowchart of FIG. 9.

Figure 6:
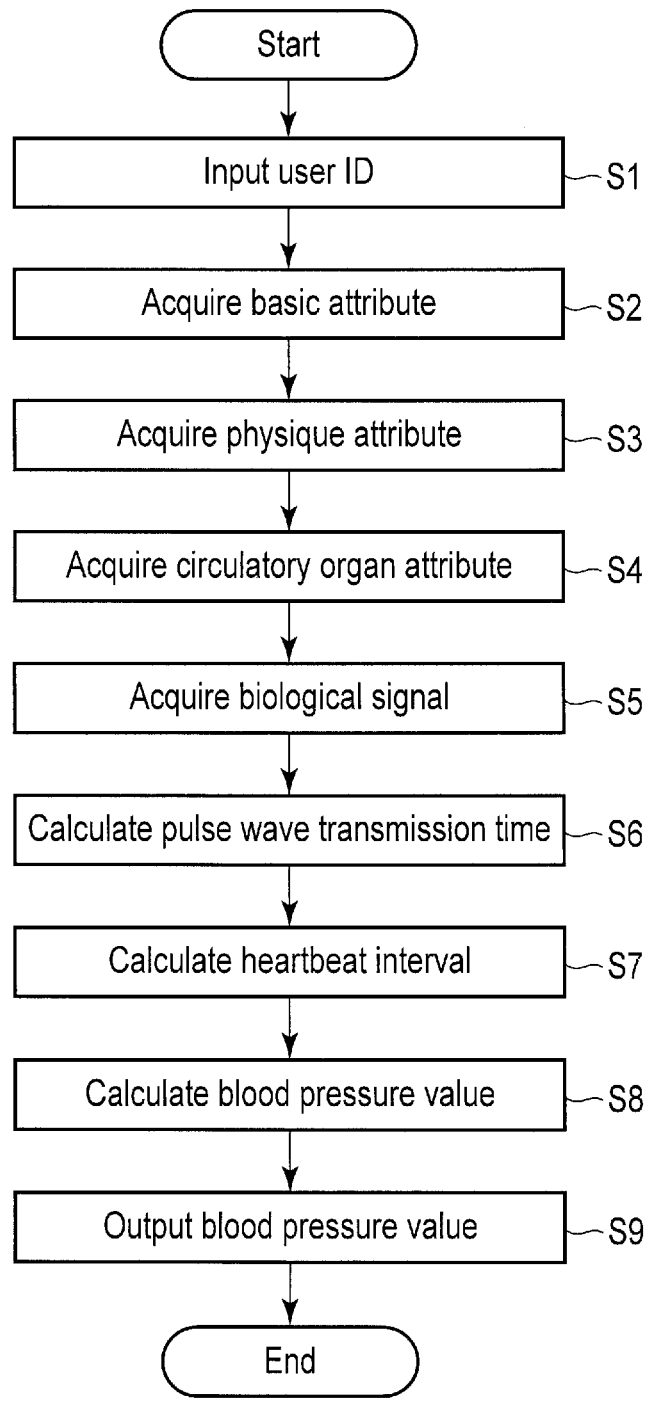
FIG. 6 is a flowchart showing an example of a procedure of the blood pressure calculation apparatus.

First, the processes of steps S11 to S13 corresponding to the above-described processes of steps S1 to S3 shown in FIG. 6 are carried out.

Then, the waveform feature calculator 201a included in the circulatory organ attribute acquisition module 201 calculates a waveform feature from a pulse wave signal (pulse waveform) measured by the first measurement module 11 (step S14).

Figure 10:
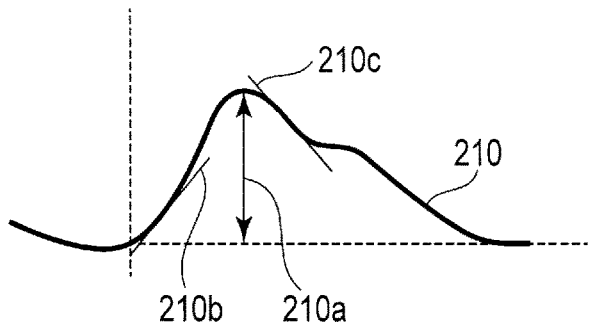
FIG. 10 is a diagram for explaining a waveform feature.

Here, a waveform feature calculated by the waveform feature calculator 201a will be described. In the present embodiment, the waveform feature calculated by the waveform feature calculator 201a is, for example, (a mean value in a measuring period of) at least one of a pulse wave height per beat in a pulse waveform, an inclination of a rise of the pulse waveform, and an inclination of a fall of the pulse waveform. FIG. 10 shows a pulse wave height in a pulse waveform, an inclination of a rise of the pulse waveform, and an inclination of a fall of the pulse waveform which are calculated as a waveform feature. For example, when a pulse waveform (pulse wave signal) 210 shown in FIG. 10 is measured by the first measurement module 11, at least one of a pulse wave height 210a, an inclination 210b of a rise, and an inclination 210c of a fall can be calculated as a waveform feature from the pulse waveform 210.

Figure 11:
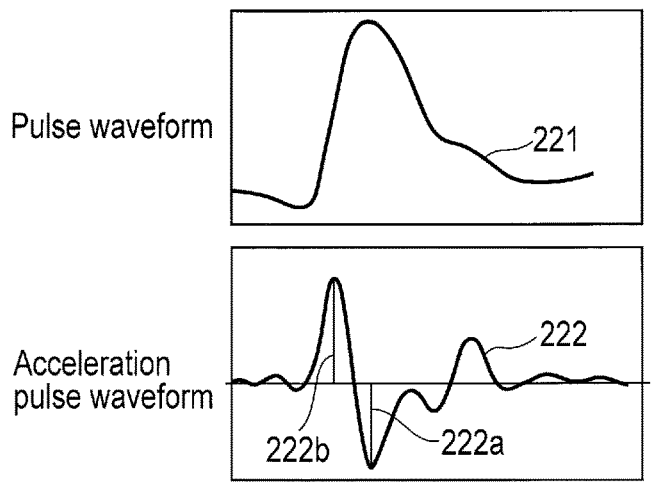
FIG. 11 is a diagram for explaining the waveform feature.

Moreover, for example, an acceleration pulse wave amplitude ratio may be used to calculate a waveform feature. Specifically, when a pulse waveform (pulse wave signal) 221 shown in FIG. 11 is measured by the first measurement module 11, an acceleration pulse waveform 222 can be obtained by differentiating the pulse waveform 221 twice. The acceleration pulse wave amplitude ratio corresponds to amplitude 222b/amplitude 222a in the acceleration pulse waveform 222. In this case, the waveform feature calculator 201a calculates a value obtained by dividing such an acceleration pulse wave amplitude ratio by a pulse wave height in a pulse waveform, as a waveform feature.

Here, in general, a pulse wave signal indicates the state of an artery of the target user 20, that is, a waveform (shape) varying according to the diameter of the artery, the elasticity of the artery, etc. Thus, the above-described pulse wave height in a pulse waveform, inclination of a rise of the pulse waveform, inclination of a fall of the pulse waveform, and value obtained by dividing an acceleration pulse wave amplitude ratio by the pulse wave height, which are calculated as waveform features, are values which reflect the state of the artery of the target user 20. That is, in the present embodiment, other values may be calculated as waveform features, as long as they reflect the state of the artery of the target user 20.

The circulatory organ attribute acquisition module 201 acquires a waveform feature calculated by the waveform feature calculator 201a in the above-described manner as a circulatory organ attribute.

Returning to FIG. 9 again, the processes of steps S15 to S17 corresponding to the above-described processes of steps S5 to S7 shown in FIG. 6 are carried out.

Next, the blood pressure value calculator 202 calculates a blood pressure value of the target user 20, using a mean pulse wave transit time (MPWTT), a mean heartbeat interval (MRRI), a basic attribute (P1), a physique attribute (P2), and a waveform feature (P3) as input (step S18). In the present embodiment, since a waveform feature is used as a substitute for a circulatory organ attribute in the above-described first embodiment, the blood pressure value of the target user 20 is calculated by the calculating expression explained in the first embodiment.

Parameters $\alpha 1$ to $\alpha 6$ of the calculating expression used in the present embodiment are, for example, values obtained in advance by carrying out a multiple regression analysis, using a waveform feature (P3), as an input variable, instead of a circulatory organ attribute such as a blood total cholesterol value. The waveform feature (P3) used for the multiple regression analysis is a value which is calculated by the waveform feature calculator 201*a* while a systelic absolute blood pressure value is measured. The parameters $\alpha 1$ to $\alpha 6$ are stored in advance in the storage 14, etc., as described above.

When the process of step S18 is carried out, the process of step S19 corresponding to the above-described process of step S9 shown in FIG. 6 is carried out.

As described above, in the present embodiment, a waveform feature in a pulse wave signal measured by the first measurement module 11 is acquired (calculated) as a circulatory organ attribute. Thus, a blood pressure value can be obtained as in the above-described first embodiment, even if the user 20 has never taken, for example, a blood test (that is, a blood total cholesterol value, etc., cannot be obtained from an external server, etc.).

The blood pressure calculation apparatus 10 can also be implemented as a combined structure of the present embodiment and the above-described first embodiment. Specifically, it is also possible to carry out the processes shown in FIG. 6 when calculating a blood pressure value of the user 20 whose blood total cholesterol value, etc., which is a blood test result, can be obtained from an external server, and carry out the processes shown in FIG. 9 when calculating a blood pressure value of the user 20 whose blood total cholesterol value, etc., cannot be obtained.

Third Embodiment

Next, a third embodiment will be described. Although it has been mainly explained in the above-described first and second embodiments that a biological signal measurement module 10*a* is provided in a blood pressure calculation apparatus 10 (that is, a fixed apparatus), the present embodiment differs from the first and second embodiments in that a biological sensor apparatus which is attached to a user 20 when used is used to measure a biological signal related to a living body of the user 20. This biological sensor apparatus is an apparatus independent of a blood pressure calculation apparatus.

That is, the blood pressure calculation apparatus according to the present embodiment is configured to calculate a blood pressure, acquiring a biological signal measured by the biological sensor apparatus from the biological sensor apparatus.

In the following description, the biological sensor apparatus and the blood pressure calculation apparatus will be referred to as a blood pressure calculation system for convenience.

Figure 12:
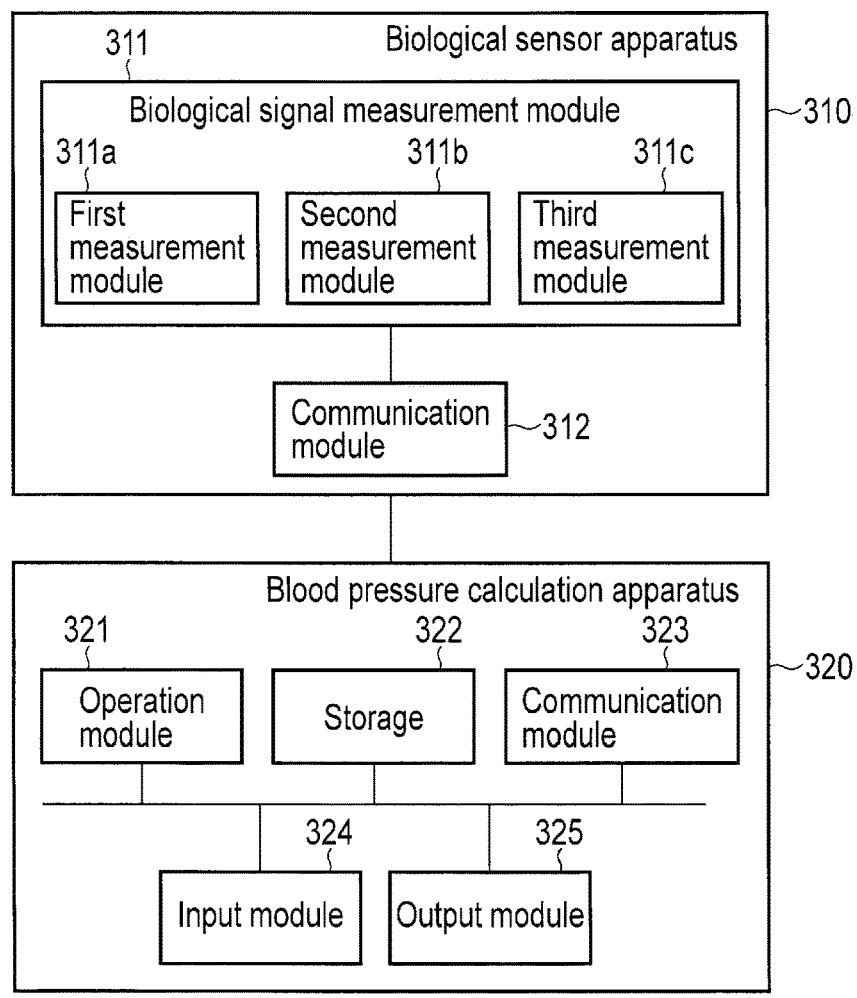
FIG. 12 is a diagram showing an example of a system configuration of a blood pressure calculation system in a third embodiment.

FIG. 12 shows an example of a system configuration of the blood pressure calculation system in the present embodiment. As shown in FIG. 12, the blood pressure calculation system includes a biological sensor apparatus 310 and a blood pressure calculation apparatus 320.

The biological sensor apparatus 310 is a small, lightweight and thin apparatus driven by a battery (for example, a built-in secondary battery). The biological sensor apparatus 310 has, for example, an elliptical shape (or a shape close to a rectangle) with the major axis of about several centimeters as shown in FIG. 13. In addition, the biological sensor apparatus 310 is used by attaching an attachment surface of the biological sensor apparatus 310 to a body surface such as the chest of the user 20 with an adhesive member 400 such as an adhesive tape. The biological sensor apparatus 310 may not be attached to the chest, but be attached by a wristband, a belt, or earphones, as long as it can measure a biological signal related to the living body of the user 20. In addition, the biological sensor apparatus 310 may also be attached to the user 20 by being sewn on clothes, etc.

The biological sensor apparatus 310 includes a biological signal measurement module 311 and a communication module 312. The biological signal measurement module 311 includes a first measurement module 311*a*, a second measurement module 311*b*, and a third measurement module 311*c*.

The first measurement module 311*a* is a measurement module corresponding to the first measurement module 11 in the above-described first and second embodiments, and includes a pulse sensor configured to measure a pulse wave signal related to a pulse wave of the user 20.

The second measurement module 311*b* is a measurement module corresponding to the above-described second measurement module 12 in the first and second embodiments, and includes an electrocardiographic sensor configured to measure an electrocardiographic signal related to the electrical activity of the heart of the user 20. Specifically, as shown in FIG. 14, two electrocardiographic electrodes 310*a* and 310*b* corresponding to the above-described electrocardiographic electrodes 12*a* and 12*b* shown in FIG. 3 are placed on the attachment surface (that is, a back surface) of the biological sensor apparatus 310. The second measurement module 311*b* can measure an electrocardiographic signal by analyzing time-series signals of a potential difference between the electrocardiographic electrodes 310*a* and 310*b* in the state where the biological sensor apparatus 310 is attached to the user 20.

The third measurement module 311*c* includes an acceleration sensor configured to measure an acceleration signal related to acceleration acting on the biological sensor apparatus 310. An acceleration signal measured by the acceleration sensor indicates, for example, acceleration produced by a movement of the trunk (that is, a body movement) of the user 20, acceleration due to gravity, etc. The acceleration sensor is, for example, a triaxial acceleration sensor (three-dimensional acceleration sensor) which can detect an acceleration signal in each axial direction of three orthogonal axes (x-, y- and z-axes).

Although it has been herein explained that the biological signal measurement module 311 includes the first measurement module 311*a* (pulse sensor), the second measurement module 311*b* (electrocardiographic sensor), and the third measurement module 311*c* (acceleration sensor), other sensors may be included in the biological signal measurement module 311. For example, a temperature sensor and an $SpO_2$ sensor may be included in the biological signal measurement module 311.

The communication module 312 is configured to communicate wirelessly through, for example, a wireless LAN. By the communication module 312, the biological sensor apparatus 310 is communicably connected to the blood pressure calculation apparatus 320, and can transmit biological signals (a pulse wave signal, an electrocardiographic signal, and an acceleration signal) measured by the biological signal measurement module 311 to the blood pressure calculation apparatus 320.

As explained in the above-described first and second embodiments, when a pulse wave signal is measured at a fingertip of the user 20, the first measurement module 311a may be attached to the ventral surface of a fingertip of the user 20 as an apparatus having, for example, a ring shape which is separate from the biological sensor apparatus 310. In this case, it suffices if the first measurement module 311a includes a structure corresponding to the light emitter 11a and the light receiver 11b described above with reference to FIG. 4, inside a housing having a ring shape. Moreover, the first measurement module 311a in this case includes a communication module corresponding to the above-described communication module 312, in order to transmit a pulse wave signal measured by the first measurement module 311a to the blood pressure calculation apparatus 320.

Although being omitted in FIG. 12, the biological sensor apparatus 310 may further includes an operation module, a storage, etc.

The blood pressure calculation apparatus 320 according to the present embodiment is implemented as, for example, an information processing apparatus such as a tablet computer, a smartphone, and a personal computer (PC).

The blood pressure calculation apparatus 320 includes an operation module 321, a storage 322, a communication module 323, an input module 324, and an output module 325.

The operation module 321, the storage 322, the communication module 323, the input module 324, and the output module 325, which are provided in the blood pressure calculation apparatus 320 according to the present embodiment, are the same as the above-described operation module 13, storage 14, communication module 15, input module 16, and output module 17 shown in FIG. 2, and thus, detailed explanations thereof will be omitted.

Figure 15:
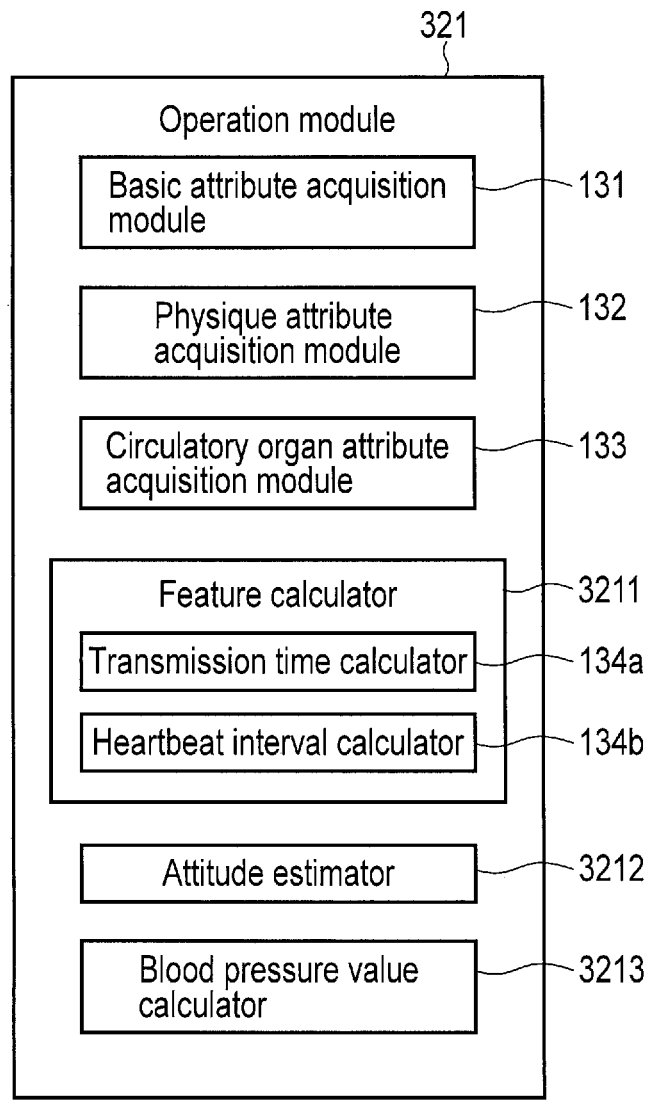
FIG. 15 is a block diagram showing an example of a functional configuration of an operation module.

FIG. 15 is a block diagram showing a functional configuration of the operation module 321 provided in the blood pressure calculation apparatus 320 according to the present embodiment. In FIG. 15, the same portions as those described above with reference to FIG. 5 are given the same reference numbers, and detailed explanations thereof will be omitted. Portions differing from those of FIG. 5 will be mainly described herein.

As shown in FIG. 15, the operation module 321 includes a feature calculator 3211, an attitude estimator 3212, and a blood pressure value calculator 3213. In the present embodiment, some or all of these modules 3211 to 3213 are implemented as software. Some or all of the modules 3211 to 3213 may be implemented as hardware, or may be implemented as a combined structure of software and hardware.

The feature calculator 3211 receives (acquires) biological signals (a pulse wave signal and an electrocardiographic signal) measured by the biological signal measurement module 311 through the communication module 323. The feature calculator 3211 calculates a feature in received biological signals. A transit time calculator 134a and a heartbeat interval calculator 134b included in the feature calculator 3211 are as described in the first embodiment, and thus, detailed explanations thereof will be omitted.

The attitude estimator 3212 receives (acquires) a biological signal (acceleration signal) measured by the biological signal measurement module 311 from the biological sensor apparatus 310 through the communication module 323. The attitude estimator 3212 estimates an attitudinal state (action) of the user based on a received acceleration signal.

The blood pressure value calculator 3213 calculates a blood pressure value of the user 20 based on a basic attribute (value) acquired by a basic attribute acquisition module 131, a physique attribute (value) acquired by a physique attribute acquisition module 132, a circulatory organ attribute (value) acquired by a circulatory organ attribute acquisition module 133, and a feature calculated by the feature calculator 3211. In this case, the blood pressure value calculator 135 calculates the blood pressure value, using parameters (values) according to the attitudinal state of the user 20 estimated by the attitude estimator 3212 as will be described later.

Figure 16:
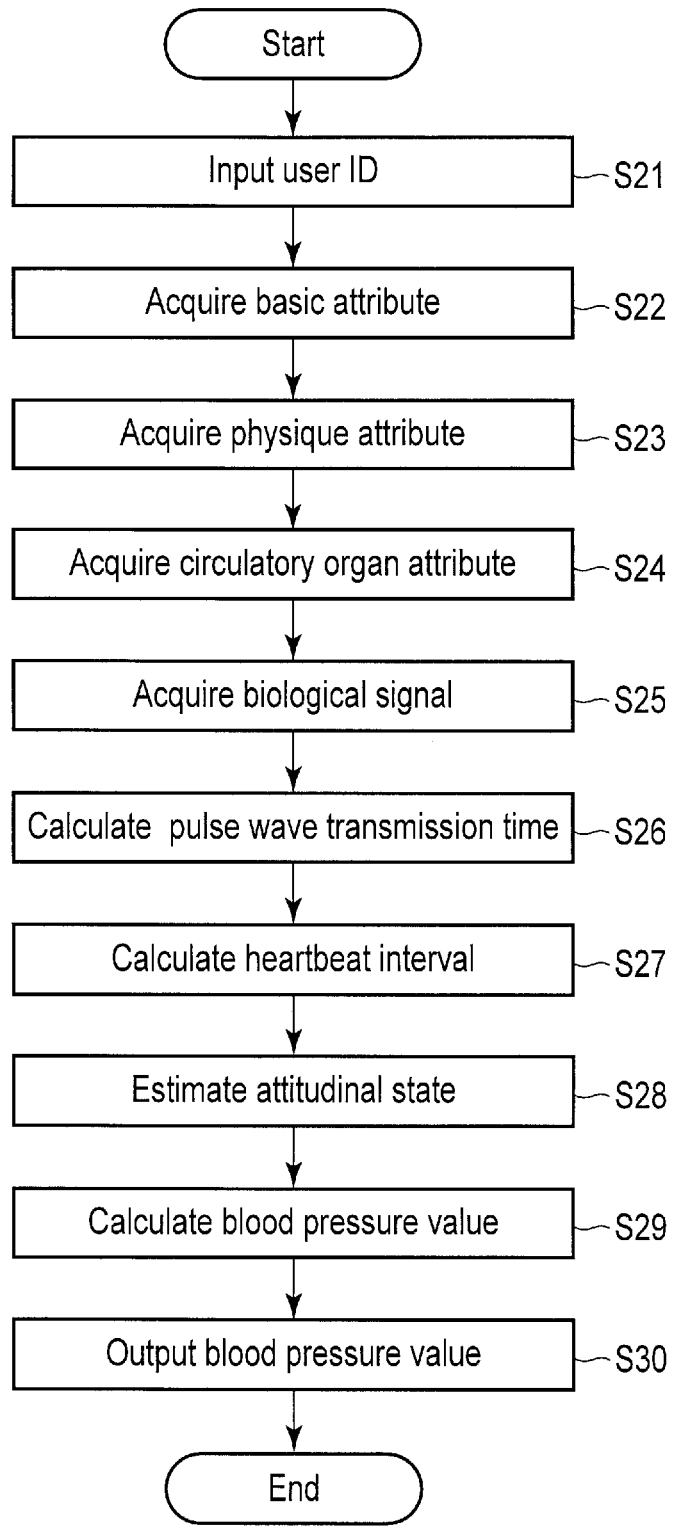
FIG. 16 is a flowchart showing an example of a procedure of the blood pressure calculation apparatus.

Next, a procedure of the blood pressure calculation apparatus 310 according to the present embodiment will be described with reference to the flowchart of FIG. 16.

First, the processes of steps S21 to S27 corresponding to the above-described processes of steps S1 to S7 shown in FIG. 6 are carried out. In step S25, biological signals (a pulse wave signal and an electrocardiographic signal) transmitted by the biological sensor apparatus 310 are acquired (received).

Here, the biological sensor apparatus 310 of the present embodiment is attached to, for example, the chest of the user (target user) 20 using the blood pressure calculation system (blood pressure calculation apparatus 320). Thus, biological signals of the target user 20 are assumed to be measured in various attitudes (states). Biological signals (a pulse wave signal and an electrocardiographic signal) measured by the biological sensor apparatus 310 may vary in accordance with the attitude of the target user 20 at the time of measurement of the biological signals.

That is, in order to improve the accuracy of a blood pressure value calculated by the blood pressure calculation apparatus 320, it is desirable to calculate the blood pressure value in consideration of the attitude of the target user 20.

Thus, the attitude estimator 3212 receives an acceleration signal transmitted by the biological sensor apparatus 310, and estimates the attitude of the target user 20 based on the acceleration signal (step S28). The attitude of the target user 20 estimated by the attitude estimator 3212 includes, for example, a seated position (or a standing position) and a supine position.

Since the acceleration sensor (third measurement module 311c) provided in the biological sensor apparatus 310 is a triaxial acceleration sensor as described above, the direction of acceleration due to gravity with respect to the biological sensor apparatus 310 can be calculated from an acceleration signal detected by the acceleration sensor. The attitude of the target user 20 is estimated based on the direction of acceleration due to gravity with respect to the biological sensor apparatus 310, which is calculated in this manner.

Specifically, with respect to the attachment surface of the biological sensor apparatus 310, axes horizontal to the attachment surface and orthogonal to each other are x- and y-axes, and an axis orthogonal to the x- and y-axes (that is, an axis in a normal direction with respect to the attachment surface) is a z-axis. When the biological sensor apparatus 310 is used, being attached to the chest of the target user 20 as shown in FIG. 13, the x-axis corresponds to an axis in a right and left direction of the target user's 20 body, the y-axis corresponds to an axis in an upward and downward direction of the target user's 20 body, and the z-axis corresponds to an axis in a forward and backward direction of the target user's 20 body, for example.

In such a case, when the direction of acceleration due to gravity with respect to the biological sensor apparatus 310 is a downward direction of the target user 20 in the y-axis, the attitude of the target user 20 is estimated to be a seated position (or a standing position). On the other hand, when the direction of acceleration due to gravity with respect to the biological sensor apparatus 310 is a backward direction of the target user 20 (that is a back direction of the user 20) in the z-axis, the attitude of the target user 20 is estimated to be a supine position.

Next, the blood pressure value calculator 3213 calculates a blood pressure value of the target user 20, using the calculating expression explained in the above-described first embodiment (step S29).

In the present embodiment, for example, it is herein assumed that parameters α1 to α6 obtained by carrying out the above-described multiple regression analysis for each attitude of the user 20 are stored in the storage 14 in advance. Specifically, in the storage 14, for example, first parameters α1 to α6 obtained when the user's attitude is a seated position (or a standing position), and second parameters α1 to α6 obtained when the user's attitude is a supine position are stored in advance.

When a blood pressure value of the target user 20 is calculated in the present embodiment, parameters α1 to α6 according to the attitude of the target user 20 estimated by the attitude estimator 3212 are used. Specifically, for example, when the attitude of the target user 20 is estimated to be a seated position, a blood pressure value of the target user 20 is calculated by applying a pulse wave transit time (MPWTT), a heartbeat interval (MRRI), a basic attribute (P1), a physique attribute (P2), and a circulatory organ attribute (P3) obtained by carrying out the above-described processes of steps S22 to S27, and the first parameters α1 to α6 according to the attitude, to the above-described calculating expression. On the other hand, for example, when the attitude of the target user 20 is estimated to be a supine position, a blood pressure value of the target user 20 is calculated by applying a pulse wave transit time (MPWTT), a heartbeat interval (MRRI), a basic attribute (P1), a physique attribute (P2), and a circulatory organ attribute (P3) obtained by carrying out the above-described processes of steps S22 to S27, and the second parameters α1 to α6 according to the attitude, to the above-described calculating expression.

In other words, in the present embodiment, parameters used to calculate a blood pressure value can be switched in accordance with the attitude of the target user 20.

When the process of step S29 is carried out, the process of step S30 corresponding to the above-described process of step S9 shown in FIG. 6 is carried out.

As described above, in the present embodiment, the blood pressure calculation apparatus 320 is communicably connected to the biological sensor apparatus 310, which is attached to the user 20 when used, an attitudinal state of the user is estimated based on an acceleration signal acquired from the biological sensor apparatus 310, and a blood pressure value of the user 20 is calculated, using parameters according to the estimated attitudinal state. In the present embodiment, according to such a structure, an error based on a change in biological signals made in accordance with the attitude of the user 20 is reduced, and a more appropriate blood pressure value can be calculated.

Although it has been explained in the present embodiment that the blood pressure calculation system includes the two apparatuses of the biological sensor apparatus 310 and the blood pressure calculation apparatus 320, the blood pressure calculation system may be implemented by the biological sensor apparatus 310 only. That is, the above-described processes shown in FIG. 16 can also be carried out by the biological sensor apparatus 310. In this case, the biological sensor apparatus 310 may be provided with a small display to display a blood pressure value of the user 20 calculated by the biological sensor apparatus 310, etc., on the display. Moreover, a blood pressure value of the user 20 calculated by the biological sensor apparatus 310, etc., may be transmitted from the biological sensor apparatus 310 to an external server.

According to at least one of the above-described embodiments, an information processing apparatus, a blood pressure calculation method, and a storage medium which enable a blood pressure value to be easily obtained can be provided.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An information processing apparatus comprising:
a storage configured to store sets of parameters for each of a supine position and a seated position of a user, each set of parameters comprising first to sixth parameters including four parameters respectively applied to each of a basic first attribute of the user, a second attribute related to a physique of the user, a blood total cholesterol value of the user, and a feature, the four applied parameters being obtained by carrying out a multiple regression analysis using the first attribute, the second attribute, the blood total cholesterol value, and the feature as input variables, and using a first blood pressure value measured in advance as a response variable; and
a processor connected to the storage and configured to:
acquire the first attribute, second attribute, blood total cholesterol value, and a biological signal related to a living body of the user;
calculate the feature in the biological signal;
estimate the seated position or the supine position as an attitude of the user, based on a direction of acceleration due to gravity detected by an acceleration sensor;
select the set of first to sixth parameters for the seated position or the supine position estimated as the attitude of the user; and
calculate a second blood pressure value of the user, by applying the selected first to sixth parameters to the acquired first attribute, second attribute, blood total cholesterol value, and the feature, according to Equation (1):

$$\alpha 1 * MPWTT + \alpha 2 * MRRI + \alpha 3 * P1 + \alpha 4 * P2 + \alpha 5 * P3 + \alpha 6, \quad (1)$$

where MPWTT is a mean pulse wave transit time of the user, MRRI is a heartbeat interval of the user, P1 is the first attribute, P2 is the second attribute, P3 is the blood total cholesterol value, and α1-α6 are the first to sixth parameters.

2. The information processing apparatus of claim 1, wherein the processor is configured to:

acquire, as the biological signal, a first pulse wave signal related to a pulse wave at a first body surface position of the user, and a second pulse wave signal related to a pulse wave at a second body surface position of the user different from the first body surface position or an electrocardiographic signal related to an electrical activity of a heart of the user; and calculate the mean pulse wave transit time or a pulse wave velocity, based on the first pulse wave signal, and the second pulse wave signal or the electrocardiographic signal.

3. The information processing apparatus of claim 1, wherein the processor is configured to:

acquire, as the biological signal, a pulse wave signal related to a pulse wave or an electrocardiographic signal related to an electrical activity of a heart of the user; and calculate the heartbeat interval or a heart rate, based on the pulse wave signal or the electrocardiographic signal.

4. The information processing apparatus of claim 1, wherein the processor is configured to acquire a pulse wave signal related to a pulse wave of the user as the biological signal.

5. The information processing apparatus of claim 1, wherein the information processing apparatus is communicably connected to a biological sensor, the biological sensor configured to be attached to the user when used and being configured to measure the biological signal, and the processor is configured to acquire the biological signal from the biological sensor.

6. The information processing apparatus of claim 1, wherein the processor is configured to acquire at least one of age, sex, and race of the user as the first attribute, or acquire at least one of a regional length of a body region of the user and an index value indicating a degree of a corpulent physique of the user as the second attribute, and the first attribute or the second attribute is acquired based on a captured image of the user.

7. The information processing apparatus of claim 6, wherein when a value of the second attribute is the regional length, the regional length includes at least one of a neck circumference, an abdominal circumference, and a hip circumference of the user.

8. The information processing apparatus of claim 6, wherein when a value of the second attribute is the index value, the index value includes at least one of a body mass index (BMI) value, a body adiposity index (BAI) value, a degree of corpulence, and body fat percentage.

9. The information processing apparatus of claim 1, wherein the processor is configured to acquire at least one of age, sex, race, disease history, drinking history, and smoking history of the user as the first attribute, acquire at least one of a regional length of a body region of the user and an index value indicating a degree of a corpulent physique of the user as the second attribute, and the first attribute, the second or the blood total cholesterol value is acquired from an external device communicably connected to the information processing apparatus.

10. The information processing apparatus of claim 1, wherein the processor is configured to acquire at least one of age, sex, race, disease history, drinking history, and smoking history of the user as the first attribute, or acquire at least one of a regional length of a body region of the user and an index value indicating a degree of a corpulent physique of the user as the second attribute.

11. The information processing apparatus of claim 1, wherein the blood total cholesterol value is a blood test result of the user, and the processor is configured to acquire the blood test result from an external device communicably connected to the information processing apparatus.

12. The information processing apparatus of claim 1, wherein the processor is configured to:

acquire the biological signal from a biological sensor configured to measure the biological signal via contact with a predetermined measured region of the user; and change a position of the biological sensor to make a relative position of the measured region with respect to a position of a heart estimated from a captured image of the user fall within a predetermined range.

13. The information processing apparatus of claim 1, comprising a display configured to display the second blood pressure value.

14. The information processing apparatus of claim 1, further comprising a transmitter configured to transmit the second blood pressure value to an external device communicably connected to the information processing apparatus.

15. A method comprising:

storing sets of parameters for each of a supine position and a seated position of a user, each set of parameters comprising first to sixth parameters including four parameters respectively applied to each of a basic first attribute of the user, a second attribute related to a physique of the user, a blood total cholesterol value of the user, and a feature, the four applied parameters being obtained by carrying out a multiple regression analysis using the first attribute, the second attribute, the blood total cholesterol value, and the feature as input variables, and using a first blood pressure value measured in advance as a response variable;

acquiring the first attribute;

acquiring the second attribute;

acquiring the blood total cholesterol value;

acquiring a biological signal related to a living body of the user;

calculating, using a processor, the feature in the biological signal;

estimating, using the processor, the seated position or the supine position as an attitude of the user, based on a direction of acceleration due to gravity detected by an acceleration sensor;

selecting, using the processor, the set of the first to sixth parameters for the seated position or the supine position estimated as the attitude of the user; and calculating, using the processor, a second blood pressure value of the user, by applying the selected first to sixth parameters to the acquired first attribute, second attribute, blood total cholesterol value, and the feature, according to Equation (1):

$$\alpha1*MPWTT+\alpha2*MRRI+\alpha3*P1+\alpha4*P2+\alpha5*P3+\alpha6, \quad (1)$$

where MPWTT is a mean pulse wave transit time of the user, MRRI is a heartbeat interval of the user, P1 is the first attribute, P2 is the second attribute, P3 is the blood total cholesterol value, and α1-α6 are the first to sixth parameters.

16. A non-transitory computer-readable storage medium having stored thereon a computer program which is executable by a computer, the computer program comprising instructions capable of causing the computer to execute functions of:
acquiring stored sets of parameters for each of a supine position and a seated position of a user, each set of parameters comprising first to sixth parameters including four parameters respectively applied to each of a basic first attribute of the user, a second attribute related to a physique of the user, a blood total cholesterol value of the user, and a feature, the four applied parameters being obtained by carrying out a multiple regression analysis using the first attribute, the second attribute, the blood total cholesterol value, and the feature as input variables, and using a first blood pressure value measured in advance as a response variable;
acquiring the first attribute;
acquiring the second attribute;
acquiring the blood total cholesterol value;
acquiring a biological signal related to a living body of the user;
calculating the feature in the biological signal;
estimating the seated position or the supine position as an attitude of the user, based on a direction of acceleration due to gravity detected by an acceleration sensor;
selecting the first to sixth parameters for the seated position or the supine position estimated as the attitude of the user; and
calculating a second blood pressure value of the user, by applying the selected first to sixth parameters to the acquired first attribute, second attribute, blood total cholesterol value, and the feature, according to Equation (1):

$$\alpha 1*\text{MPWTT}+\alpha 2*\text{MRRI}+\alpha 3*P1+\alpha 4*P2+\alpha 5*P3+\alpha 6, \qquad (1)$$

where MPWTT is a mean pulse wave transit time of the user, MRRI is a heartbeat interval of the user, P1 is the first attribute, P2 is the second attribute, P3 is the blood total cholesterol value, and α1-α6 are the first to sixth parameters.

* * * * *